(12) United States Patent
Knipfer et al.

(10) Patent No.: US 8,718,774 B2
(45) Date of Patent: May 6, 2014

(54) HOUSINGS FOR IMPLANTABLE MEDICAL DEVICES AND METHODS FOR FORMING HOUSINGS

(75) Inventors: Michael A. Knipfer, Maple Grove, MN (US); John M. Edgell, Plymouth, MN (US); Robbie L. Halvorson, Oakdale, MN (US); Lawrence D. Swanson, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 497 days.

(21) Appl. No.: 12/708,059

(22) Filed: Feb. 18, 2010

(65) Prior Publication Data

US 2010/0274309 A1 Oct. 28, 2010

Related U.S. Application Data

(60) Provisional application No. 61/172,025, filed on Apr. 23, 2009.

(51) Int. Cl.
*A61N 1/375* (2006.01)

(52) U.S. Cl.
CPC .................................... *A61N 1/375* (2013.01)
USPC ................... 607/36; 607/2; 164/47; 164/137

(58) Field of Classification Search
USPC ...................................................... 607/2, 36
See application file for complete search history.

(56) References Cited

U.S. PATENT DOCUMENTS

| | | | |
|---|---|---|---|
| 4,314,562 A * | 2/1982 | Ware | ............................... 607/36 |
| 5,288,344 A | 2/1994 | Peker et al. | |
| 5,735,975 A | 4/1998 | Lin et al. | |
| 5,873,899 A | 2/1999 | Stutz, Jr. et al. | |
| 6,010,803 A | 1/2000 | Heller, Jr. et al. | |
| 6,306,141 B1 | 10/2001 | Jervis | |
| 6,445,948 B1 * | 9/2002 | Somdahl et al. | ................... 607/2 |
| 6,620,264 B2 | 9/2003 | Kundig et al. | |
| 7,069,080 B2 | 6/2006 | Bardy et al. | |
| 7,082,336 B2 | 7/2006 | Ransbury et al. | |

(Continued)

FOREIGN PATENT DOCUMENTS

WO WO-2007/136657 A1 11/2007

OTHER PUBLICATIONS

PCT International Search Report and Written Opinion, From International Application No. PCT/US2010/024766, corresponding to U.S. Patent Application No. 61/172,025, mailed Mar. 15, 2011, 1-18 Pgs.

(Continued)

*Primary Examiner* — Carl H Layno
*Assistant Examiner* — Jon Eric C Morales
(74) *Attorney, Agent, or Firm* — Pauly, DeVries Smith & Deffner LLC

(57) ABSTRACT

Described herein is an implantable medical device and methods for making a device that includes a metal housing a molding process. In one embodiment, the housing includes a header attachment element extends from the housing. In another embodiment, the implantable medical device includes a header attachment surface comprising one or more header retaining features configured to secure a connector header to the header attachment surface. In another embodiment, the housing includes one or more structural elements extending from and integrally molded with the interior surface of the first or second portions of the housing. Also disclosed are methods of making the implantable medical device.

17 Claims, 10 Drawing Sheets

(56) References Cited

U.S. PATENT DOCUMENTS

| | | |
|---|---|---|
| 7,110,819 B1 | 9/2006 | O'Hara |
| 7,194,309 B2 | 3/2007 | Ostroff et al. |
| 7,270,679 B2 | 9/2007 | Istephanous et al. |
| 7,308,313 B1 | 12/2007 | Lim et al. |
| 7,351,921 B1 | 4/2008 | Haller et al. |
| 7,376,466 B2 | 5/2008 | He et al. |
| 7,383,085 B2 | 6/2008 | Olson |
| 7,428,437 B2 | 9/2008 | Bardy et al. |
| 2002/0138114 A1* | 9/2002 | Gramse ............ 607/37 |
| 2004/0082977 A1* | 4/2004 | Engmark et al. ........ 607/36 |
| 2004/0230250 A1 | 11/2004 | Neumann et al. |
| 2007/0239222 A1* | 10/2007 | Sprain et al. ............ 607/37 |
| 2008/0139031 A1 | 6/2008 | Ries et al. |
| 2008/0139053 A1 | 6/2008 | Ries et al. |

OTHER PUBLICATIONS

Merhar, Robert J., "Metal Injection Molding: An Overview," *Medical Device Link. The Online Information Source for the Medical Device Industry* May 1996, pp. 1-4.

"LIQUIDMETAL® Medical Devices," *LIQUIDMETAL® Technologies* http://www.liquidmetal.com/applications/dsp.medical/asp Jul. 18, 2008, 1 page.

"Metal Injection Molding (MIM)," *GKN Sinter Metals* 2010, 1 page.

* cited by examiner

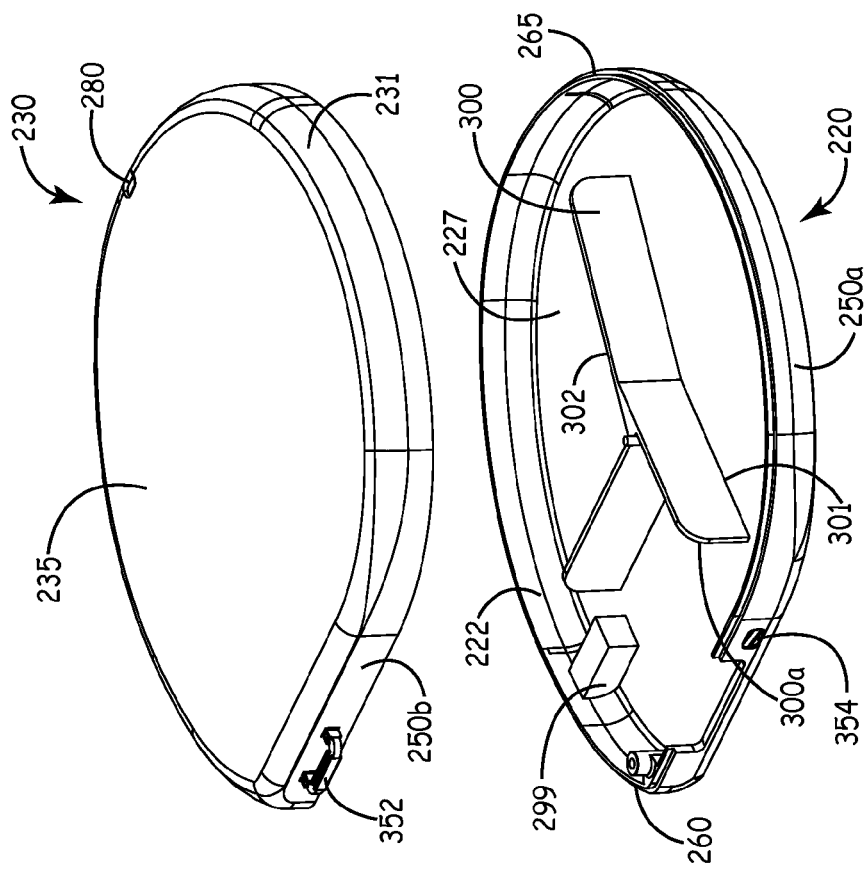
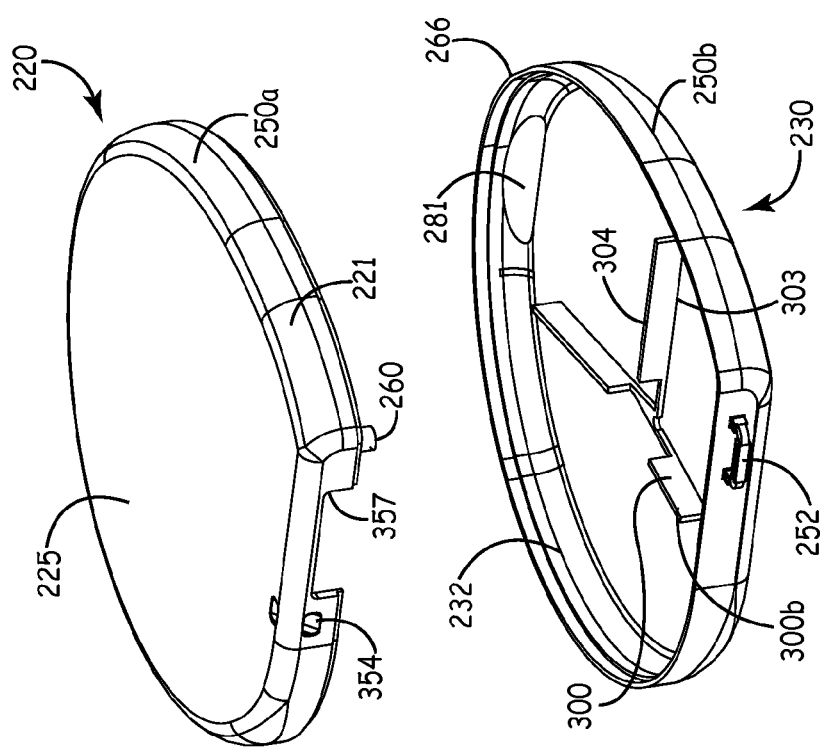

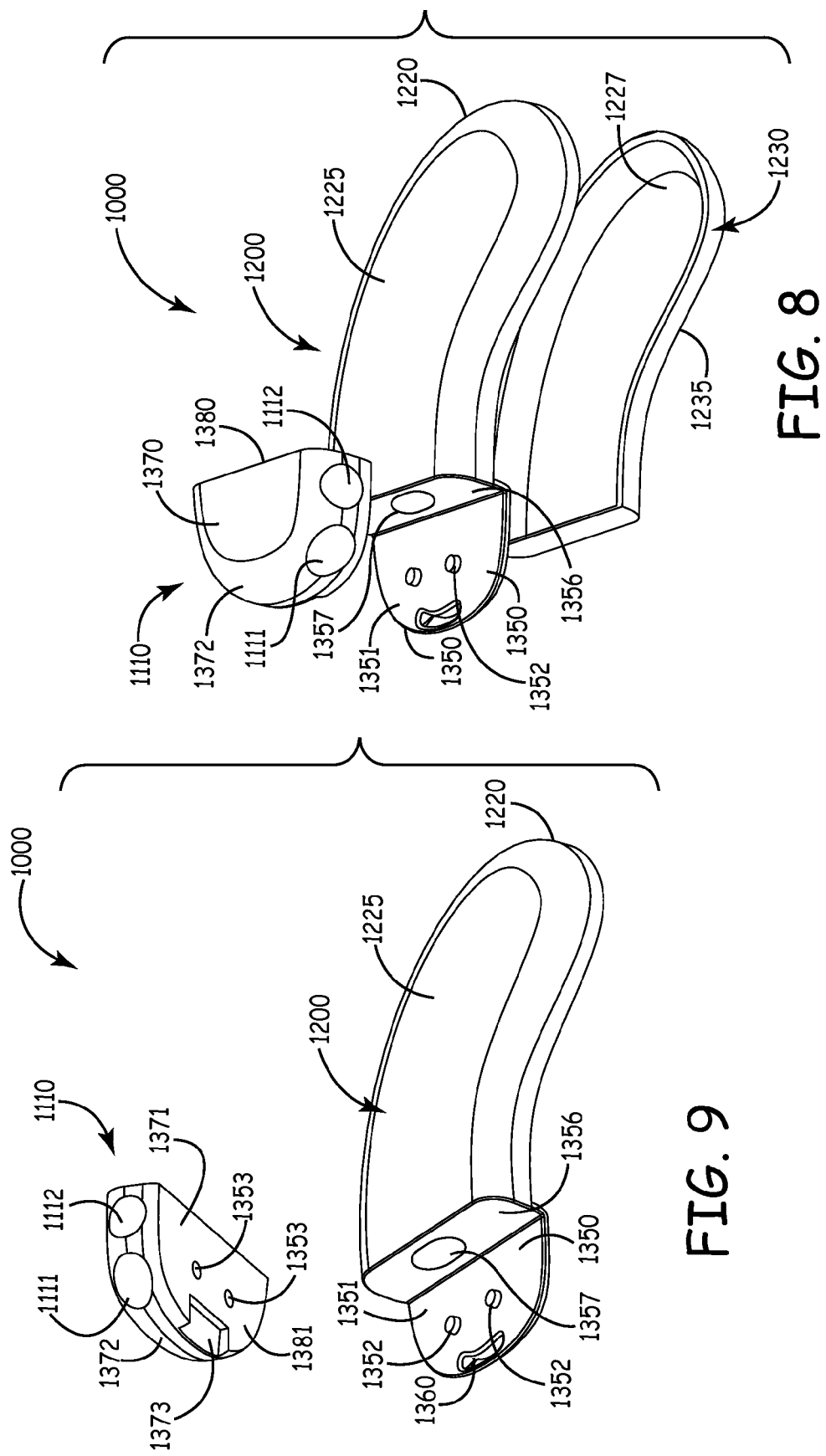

HOUSINGS FOR IMPLANTABLE MEDICAL DEVICES AND METHODS FOR FORMING HOUSINGS

This application claims the benefit of U.S. Provisional Application No. 61/172,025, filed Apr. 23, 2009, the contents of which are herein incorporated by reference.

FIELD OF THE INVENTION

The invention described herein relates to implantable medical devices, and more particularly to housings for cardiac rhythm management devices.

BACKGROUND OF THE INVENTION

Implantable medical devices (IMDs) are commonly used to provide treatment to patients. Implantable medical devices can include cardiac rhythm management (CRM) devices, including pacemakers and Implantable Cardioverter Defibrillators (ICDs). In general, CRM devices deliver electrical stimuli to a target tissue via a lead wire having one or more electrodes disposed in or about the target tissue. The lead wire is typically connected to a pulse generator contained within a housing. In addition to the pulse generator, the housing can also contain other system components. Typically, the housing is formed by stamping the desired shaped components from a sheet of metal.

SUMMARY OF THE INVENTION

Described herein is an implantable medical device that includes a metal housing having a first portion, second portion, a header attachment element and an electronics package configured to be disposed within the housing, in one embodiment. The first portion includes a base and one or more sidewalls, each with an interior surface and an exterior surface, wherein the interior surfaces of the base and sidewalls define a cavity. The second portion is configured to enclose the cavity defined by the first portion when the housing is assembled. The header attachment element extends from the first or second portion of the housing, and includes a header attachment surface with one or more header attachment structures configured to mate with a connector header. In one embodiment, the header attachment element is integrally molded with the first or second portion of the housing. In another embodiment, the implantable medical device includes a header attachment surface comprising one or more header retaining features configured to secure a connector header to the header attachment surface. In one embodiment, one or more header retaining features include a handle-shaped projection. In another embodiment, the housing includes one or more structural elements extending from and integrally molded with the interior surface of the first or second portions of the housing. Also disclosed are methods of making the implantable medical device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

FIG. 3 is an exploded perspective view of one embodiment of a housing for an implantable medical device having an internal structural element.

FIG. 4 is an exploded perspective view of the embodiment of a housing shown in FIG. 3 in which the elements have been rotated 180 degrees.

FIG. 8 is an exploded view of an alternate embodiment of a device described herein.

FIG. 9 is an exploded view of the device of FIG. 8.

Figure 1:
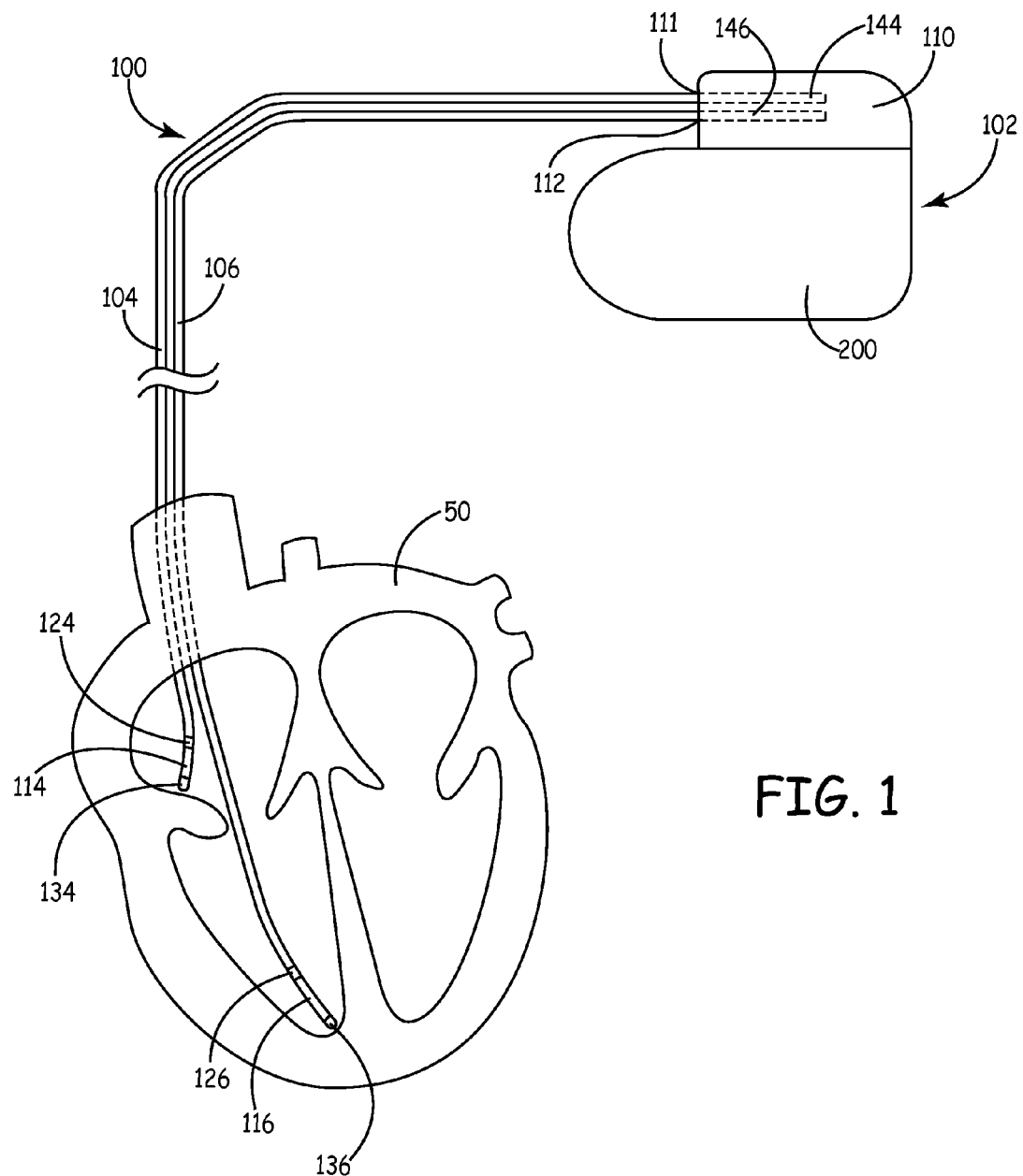
FIG. 1 is a schematic view of an implanted medical device as described herein shown in conjunction with a heart.

While the invention is susceptible to various modifications and alternative forms, specifics thereof have been shown by way of example and drawings, and will be described in detail. It should be understood, however, that the invention is not limited to the particular embodiments described. On the contrary, the intention is to second modifications, equivalents, and alternatives falling within the spirit and scope of the invention.

DETAILED DESCRIPTION OF THE EMBODIMENTS

Implantable medical devices for cardiac rhythm management (CRM) include devices such as pacemakers and Implantable Cardioverter Defibrillators (ICDs). Typically implantable medical devices such as pacemakers and ICDs are constructed using stamped metal enclosures or machined components. However, the use of stamped metal processes can limit the design of the device since the designer must adhere to the capabilities of the stamped metal process. Furthermore, manufacturing must deal with the inconsistency of the stamped metal forming process and the impact on yield.

Described herein is an implantable medical device constructed using a molding process and a methods for making the implantable medical device. The device and method are especially applicable to the field of implantable medical devices that enclose electronics components. One context in which the devices and methods described herein can be particularly applied is cardiac rhythm management devices.

By molding the housing, various manufacturing, inspecting, and assembly costs are reduced. As used herein, the term "molding" refers to a process of manufacturing in which a flowable material is shaped using a pattern or mold. Many molding processes are known and include, but are not limited to: injection molding, compression molding, transfer molding, extrusion molding, rotational molding, and the like.

In one embodiment, the flowable material used in the molding process is a conductive material, such as a metal or metal alloy. In another embodiment, the flowable material used in the molding process is a non-amorphous or crystalline metal or metal alloy. As used herein, the terms "non-amorphous" or "crystalline" metal or metal alloy refers to a metallic material whose atomic structure is crystalline or ordered. In another embodiment, the metal is an amorphous metal alloy. As used herein, the term "amorphous metal alloy" refers to a structural metallic material, capable of bearing a mechanical load or resisting superimposed mechanical stress, whose atomic structure, in contrast to conventional metals, is non-crystalline or disordered (e.g., no discernable patterns exist in the atomic structure of the alloy) in the solid state. Amorphous metal alloys can also possess unique physical and magnetic properties that combine strength and hardness with flexibility and toughness. An amorphous metal alloy is a combination of two or more materials. Methods for producing amorphous metals are known and include physical vapor deposition, solid-state reaction, ion irradiation, melt spinning, electromagnetic induction, and mechanical alloying.

Materials possessing sufficient hardness that are suitable for molding include numerous biocompatible materials such as medical metals and alloys. Examples of such materials include, but are not limited to, stainless steel, titanium, aluminum, zirconium, tantalum, nickel, molybdenum, niobium, cobalt, tungsten, platinum, palladium, gold, silver, copper chromium, vanadium, hafnium, zinc, iron and other metals, alloys or mixtures thereof.

The molding process allows a number of design features to be easily included in the device that may not be possible with stamped metal. Various embodiments of an implantable medical device as described herein may provide one or more of the following advantages: eliminating production steps; eliminating inspection steps; and the provision of additional features without significant additional manufacturing, inspection, and assembly steps.

FIG. 1 is a schematic view of an implantable medical device 100 shown in conjunction with a heart 50. The device 100 generally includes a hermetically sealed housing 200 that encases the electronics for the device 100, a connection header 110, one or more leads 104, 106 and one or more electrodes 124, 134, 126, 136. The leads 104, 106 electrically couple a pulse generator 102, located within the housing 200, with the heart 50. Distal ends 114, 116 of the electrical stimulation leads 104, 106 have one or more electrodes 124, 134, 126, 136, which are disposed in operative relation to the patient's heart 50. The leads 104,106 can include one or more of the following electrodes: cardioversion/defibrillation electrodes, pacing electrodes and/or sense electrodes. Typically, the header 110 defines one or more apertures 111, 112 configured to receive a proximal end 144, 146 of a lead 104,106. The apertures 111, 112 include one or more electrical contacts (not shown) that extend from the header 110 to the internal circuitry (not shown). Typically, wires made from a conductive material pass from the pulse generator 102 within the housing 200 to one or more connector blocks (not shown) within the header 110.

When in use, the device 100 is implanted in the patient. In operation, the pulse generator 102 may generate pacing pulses and/or therapeutic shocks which are delivered from the header assembly 110 through the leads 104, 106 and to the heart 50. In many embodiments, the leads 104, 106 include a material that is electrically conductive in order to deliver the pacing pulses or therapeutic shocks.

Housing

One function of the housing 200 is to provide a protective barrier between the system components enclosed within its confines and the surrounding environment. The housing 200 is typically formed of a material that is conductive, biocompatible, capable of sterilization and capable of being hermetically sealed. Furthermore, the housing 200 provides sufficient structural integrity to protect the system components from damage. According to the invention described herein, the housing 200 can be formed by a molding process.

Figure 14:
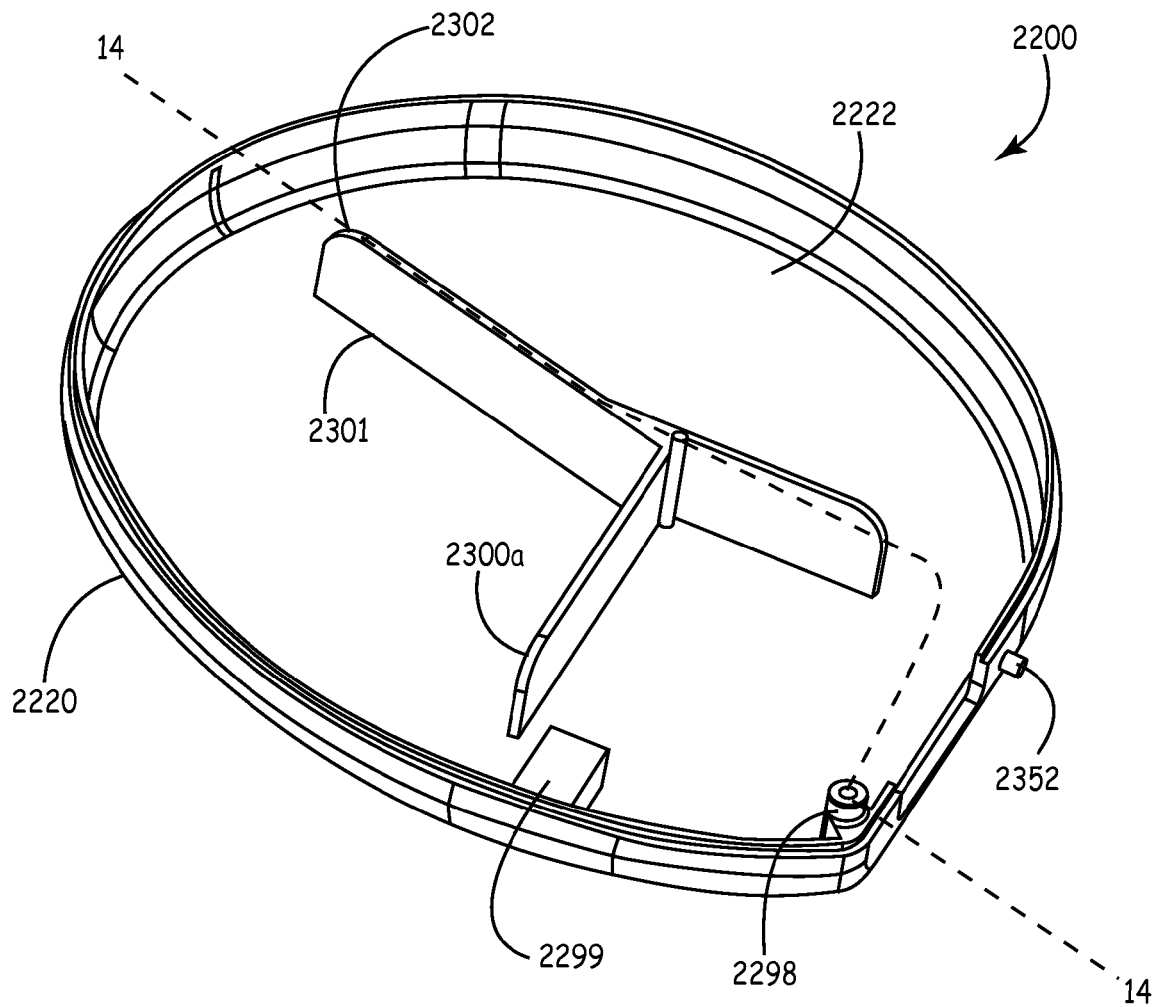
FIG. 14 is a top perspective view of an alternate embodiment of a housing described herein showing a structural element.
Figure 16:
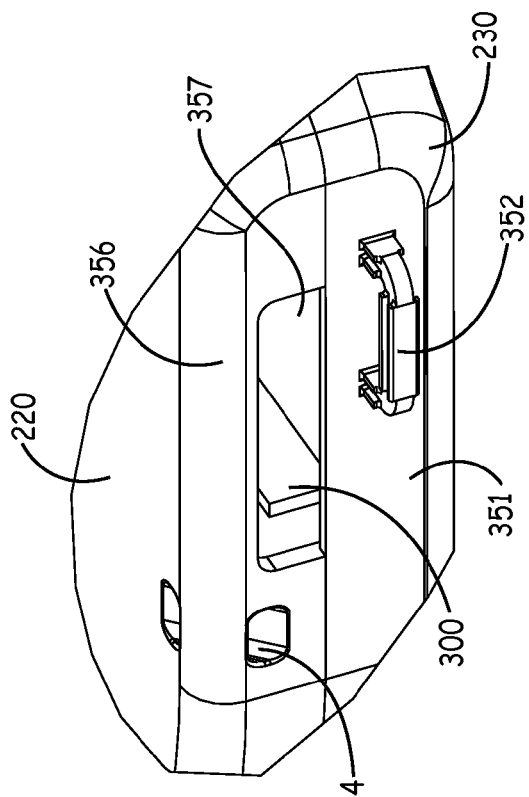
FIG. 16 is a close up view of Detail B shown in FIG. 15.
Figure 17:
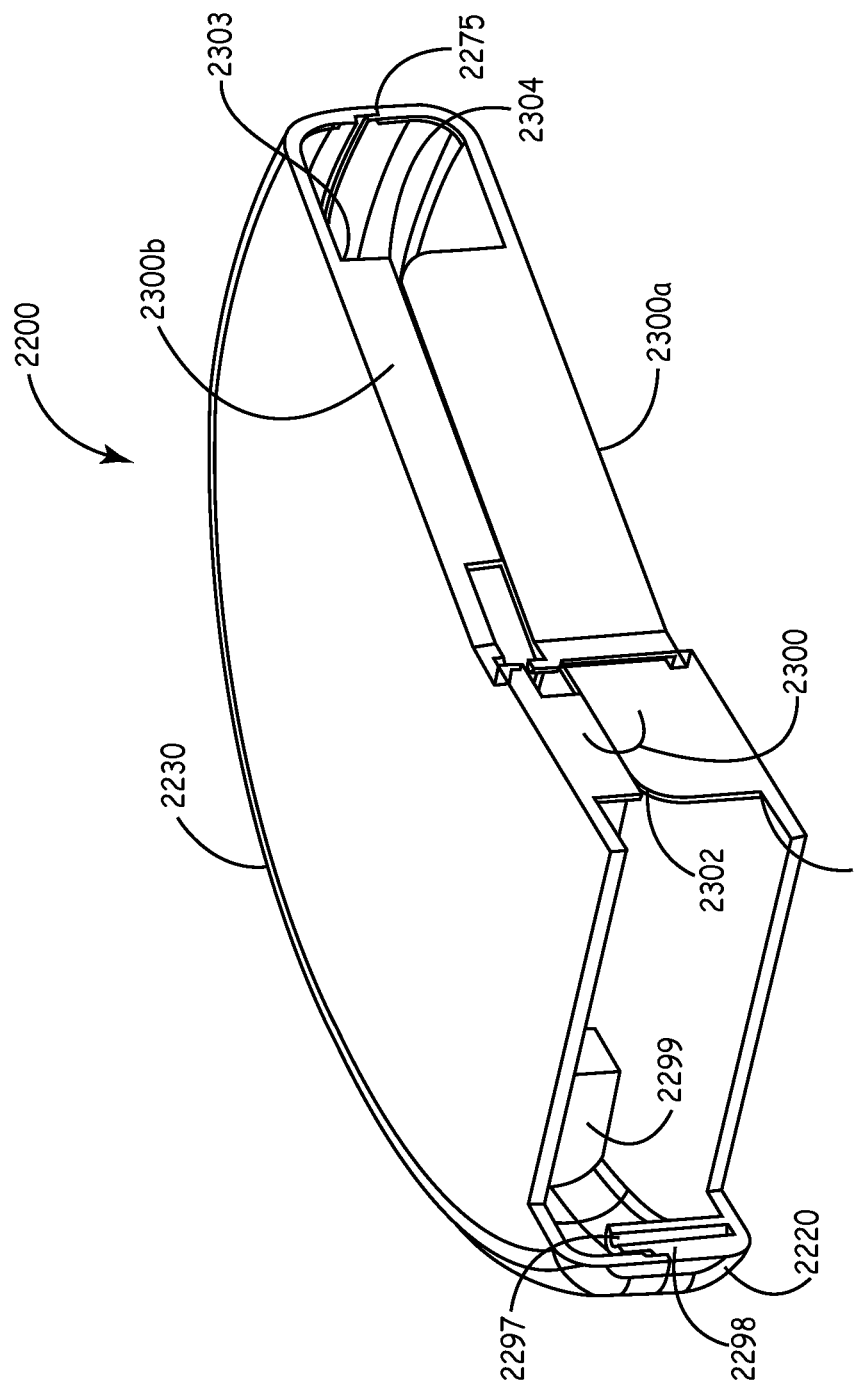
FIG. 17 is a cross-sectional view of a housing taken along line 17-17 in FIG. 15 showing a structural element as described herein.

A first embodiment of a housing is shown in FIGS. 2-6, 15 and 16. A second embodiment of a housing is shown in FIGS. 8-11. A third embodiment of a housing is shown in FIGS. 14 and 17. In the discussion of the various embodiments herein, the final three digits for the reference numbers are the same for similar elements. Any discussion herein of an element having the last three digits in common with a similar element in another embodiment is meant to apply to the similarly numbered elements in the other embodiments.

In the embodiment shown in FIGS. 2-6 and 15-16, the housing 200 generally includes a first portion (or half) 220 and a second portion (or half) 230 joined by a perimeter sidewall 250. In one embodiment, the housing 200 has substantially planar top 235. In another embodiment, the housing has a substantially planar base 225. In the embodiment shown in FIGS. 2-6 and 15-16, the perimeter sidewall 250 is curved. As used herein, the term "substantially planar" means that, for the most part, the surfaces are flat (e.g., more than 50% or more than 75% of the surface area is planar). For example, when the top 235 and base 225 surfaces are flat, the housing 200 may be generally rectangular or square when viewed in cross section even though the housing 200 will typically have rounded corners or a curved sidewall, such that the cross-sectional view is not completely rectangular or square. It is also envisioned that the top 235 and bottom 225 surfaces may include some amount of curvature or projections, protrusions or indentations in some embodiments. In the embodiment shown in FIG. 2, the generally planar top 235 or bottom 225 surfaces are generally opposing surfaces and are substantially parallel to one another. As used herein, the term "substantially parallel" means that, for the most part, the surfaces are parallel. However, it is envisioned that some degree of convergence or divergence of the two surfaces may be desirable in some embodiments. Additionally, it may be desirable to have a housing 200 with a more circular or oval cross section. Typically, the two portions 220, 230 of the housing are laser seam welded together at a seam or weld line 275 extending around the periphery of the sidewall 250.

Figure 2:
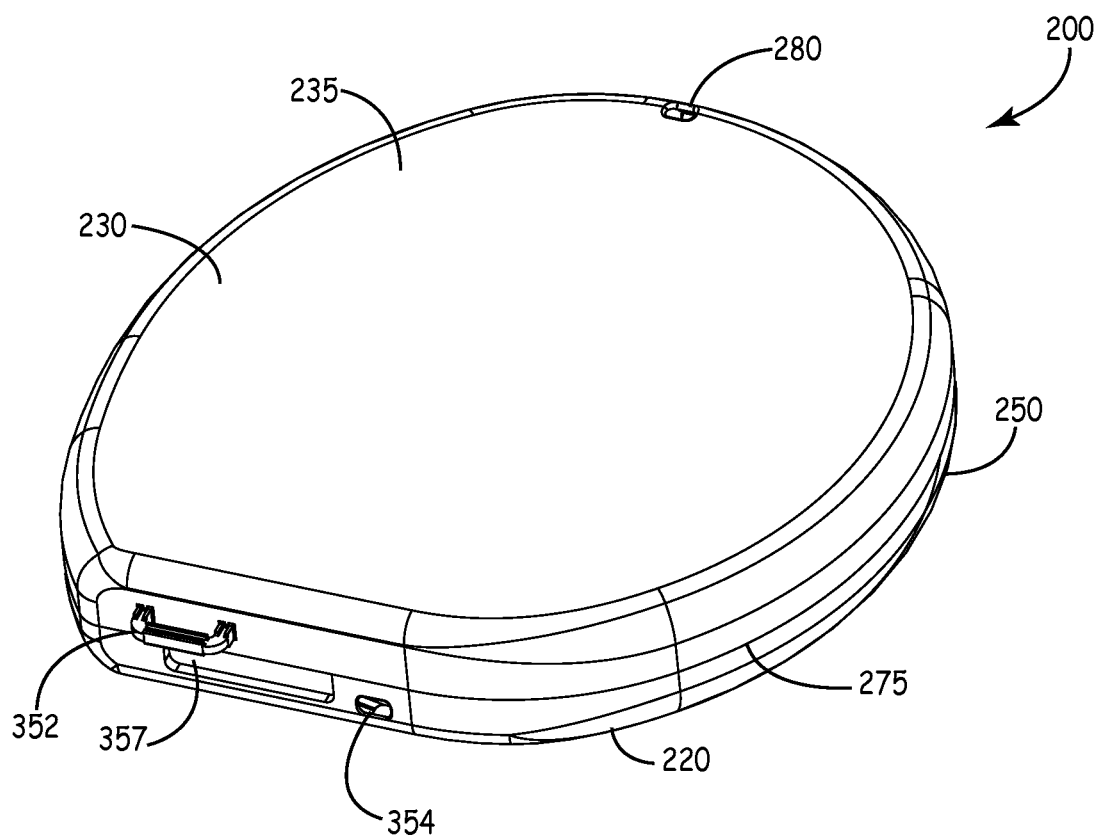
FIG. 2 is a perspective view of a housing for an implantable medical device as described herein.
Figure 6:
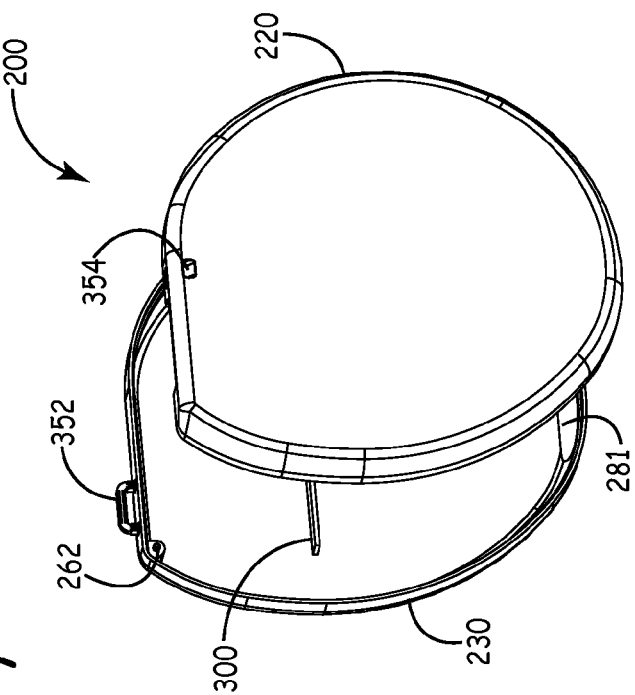
FIG. 6 is an exploded view of the housing shown in FIG. 5, in which the elements have been rotated 180 degrees.
Figure 7:
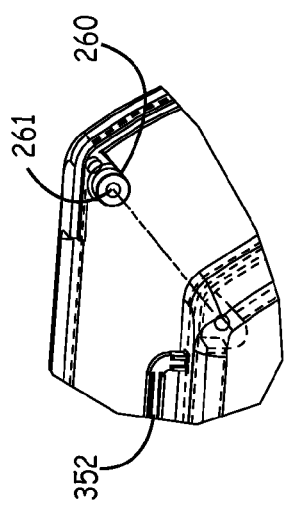
FIG. 7 is a partial close up view the positioning element of the housing shown in FIG. 5.
Figure 5:
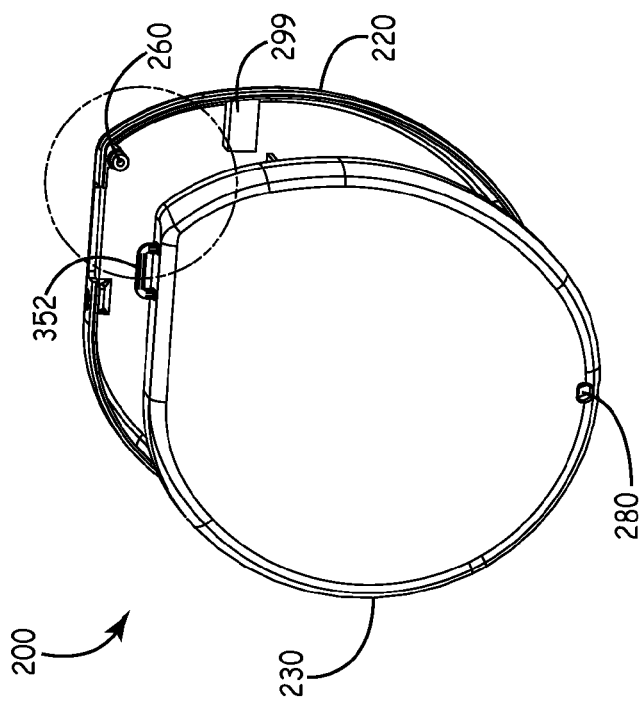
FIG. 5 is an exploded view of the housing shown in FIG. 3.
Figure 10:
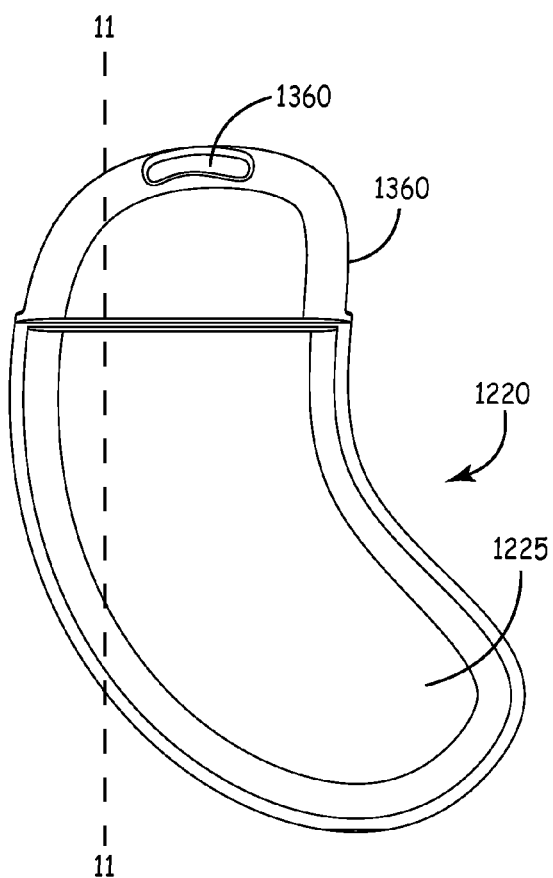
FIG. 10 is a view the device of FIG. 8 shown from the bottom.
Figure 11:
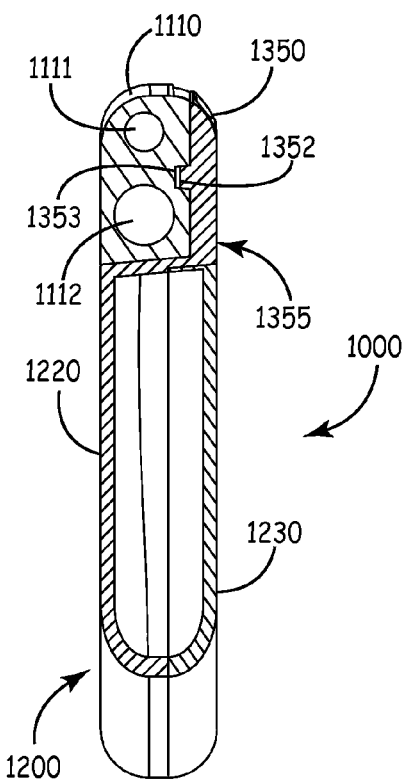
FIG. 11 is a cross sectional view of the device shown in FIG. 10 taken along line 11-11 in FIG. 10.

FIG. 2 is a perspective view of an embodiment of the housing 200 for an implantable medical device 100. As shown in FIGS. 3 & 4, the first portion 220 includes substantially parallel opposing inner 222 and outer 221 surfaces, a base 225 and one or more sidewalls 250a extending upwardly from the base 225 to define a cavity 227. The sidewalls 250a terminate in a peripheral edge 265 disposed between the inner 222 and outer 221 surfaces of the sidewalls that define an opening in the first portion 220. The thickness of the housing sidewall 250 can vary, but in general it is at least about 0.1 mm thick, more typically at least about 0.5 mm thick and generally no more than about 1.0 mm thick, or no more than about 2.5 mm thick.

Similarly, the second portion 230 includes substantially parallel opposing inner 232 and outer 231 surfaces and is configured to enclose the cavity 227 defined by the first portion 220 when the housing 200 is assembled. In one embodiment, the second portion 230 includes one or more sidewalls 250b extending from the top 235. In one embodiment, the sidewalls 250b of the second portion 230 generally mirror the shape of the first portion 220 sidewalls 250a such that the one or more second portion 230 sidewalls 250b are configured to mate with the first portion 220 sidewalls 250a when the housing 200 is assembled. The sidewalls 250b of the second portion 230 terminate in a peripheral edge 266 disposed between the inner 232 and outer 231 surfaces of the sidewall 250b. In one embodiment, the second portion 230 sidewalls 250b have a height that is less than the height of the first 220 portion sidewalls 250a. In another embodiment, the second portion 230 sidewalls 250b have a height that is greater than the height of the first 220 portion sidewalls 250a. As used in the context of the first portion 220 sidewall 250a, the term "height" refers to the shortest linear distance between the top (or plane defined by the top) surface 225 of the housing 200 to the peripheral edge 265 of the sidewall 250a. Similarly, as used in the context of the second portion 230 sidewall 250b, the term "height" refers to the shortest linear distance between the base (or plane defined by the base) surface 235 of the housing 200 to the peripheral edge 266 of the sidewall 250b. In another embodiment, the second portion 230 sidewalls 250b have a height that is substantially the same as the first portion 220 sidewalls 250a. In an alternate embodiment (not shown), the second portion 230 does not include a sidewall, but rather includes a protrusion extending from the interior surface 232 of the top 235 that is spaced from the edge of the second portion 230 and follows the perimeter of the second portion 230. In this embodiment, the first portion 220 sidewall 250a is configured to physically overlap and rest externally to the protrusion such that the peripheral edge 265 of the first portion 220 engages the interior surface 232 of the top 235 when the housing 200 is assembled.

In general, the implantable medical device 100 can be constructed having any suitable size and shape. However, the external surfaces 221, 231 are generally smooth with the rounded corners where the sidewalls 250a, 250b join the top 225 and base 235 of the housing 200. Additionally, the exterior surface of the housing is generally void of appendages or protrusions. Smoothing the external surface reduces the coefficient of friction of the housing 200 and helps the housing 200 to advance through the subcutaneous tissues during implantation. In addition to reducing abrasion and inflammation associated with insertion and advancement of the device, after implantation a smooth surface will reduce inflammation and soreness, increasing wearability and comfort.

In one embodiment, the housing 200 includes one or more suture anchoring locations 280. In contrast to many of the currently available devices, in which placement of suture anchoring locations 280 is limited by the stamping technology used to fabricate the device 100, the molding process used to form the housing 200 described herein allows for the placement of one or more suture anchoring locations 280 in the housing 200 as shown in FIGS. 2-6.

In general, a suture anchoring location 280 is defined by an opening in the housing 200 through which a suture and a suture needle can be passed. However, it is important that the opening in the housing 200 remain separate from the interior cavity 227 enclosed by housing 200 so that the housing 200 can be hermetically sealed to protect the system components from the external environment. In one embodiment, a first opening is defined in the top surface 235 of the first portion 220 of the housing 200 and extends to a second opening defined in a sidewall 250a of the first portion 220. To maintain the integrity of the hermetic seal, the first portion 220 of the housing may include a barrier 281 positioned on the internal surface 222 of the first portion of the housing 220 opposite the openings to seal the suture anchoring location 280 off from the cavity 227 defined by the housing 200.

In another embodiment, one or more similar suture anchoring locations 280 can be included in the second portion 230 of the device, if desired. In an alternate embodiment (not shown), the suture anchoring location is defined by a first opening in a sidewall 250a that extends to a second opening located in the same sidewall 250a of the device. Again, a similar configuration for a suture anchoring location can be included in the second portion 230 of the housing 200.

The housing 200 is shown in FIGS. 2-6 includes one or more positioning elements 260 configured to maintain the relative alignment of the first 220 and second 230 portions of the header 200 when the device is assembled. In one embodiment (shown in FIG. 5), the positioning element 260 includes one or more projections 262 extending from one half of the housing 200 and one or more corresponding apertures 261 in the other half of the housing 200, wherein the apertures 261 are configured to receive the projections 262 when the housing 200 is assembled. It is conceivable that one half of the housing 200 could include one or more apertures 261 and one or more projections 262, wherein each of the one or more apertures 261 and projections 262 in the first half of the housing 200 have mating apertures 261 and projections in the second half of the housing 200. In the embodiment shown in FIG. 4, the first portion 220 of the housing 200 includes one or more pin bosses 260 extending from an internal surface 222, wherein the one or more pin bosses 260 define an aperture 261. The second portion 230 of the housing 200 includes one or more corresponding pins 262 extending from an internal surface 232. Although the embodiment shown in FIG. 4 shows the pin 262 and pin boss 260 located proximate the sidewall of the housing 200, it is envisioned that the positioning element 260 can be located at any suitable location on the housing 200, for example, at the center of the housing 200 or at any position between the center and the perimeter of the housing 200.

In one embodiment, the housing 200 is designed to be positioned in close proximity to the patient's heart, for example, between the 4th and 5th ribs or between the 5th and 6th ribs. Therefore, it may be desirable in one embodiment to have a housing 200 that is long, thin, and curved to conform to the natural curvature of the patient's ribcage within the thorax, although the radius of curvature need not be uniform throughout the housing. FIGS. 8-11 show an embodiment of a device 1000 having a curved housing 1200. Similar to the previously described embodiment, the first portion 1220 of the device 1000 is configured to mate with the second portion 1230 of the device to form a hermetically sealed cavity 1227 configured to house one or more system components. Even though the disclosure herein focuses on a two-piece housing, it is envisioned that single-piece and multi-piece housings having more than two housing sections are possible. Furthermore, other locations for implanting the device 100 are possible and, consequently, other shapes or configurations for the housing 200 may be desirable.

Weld Line

Figures 12, 13:
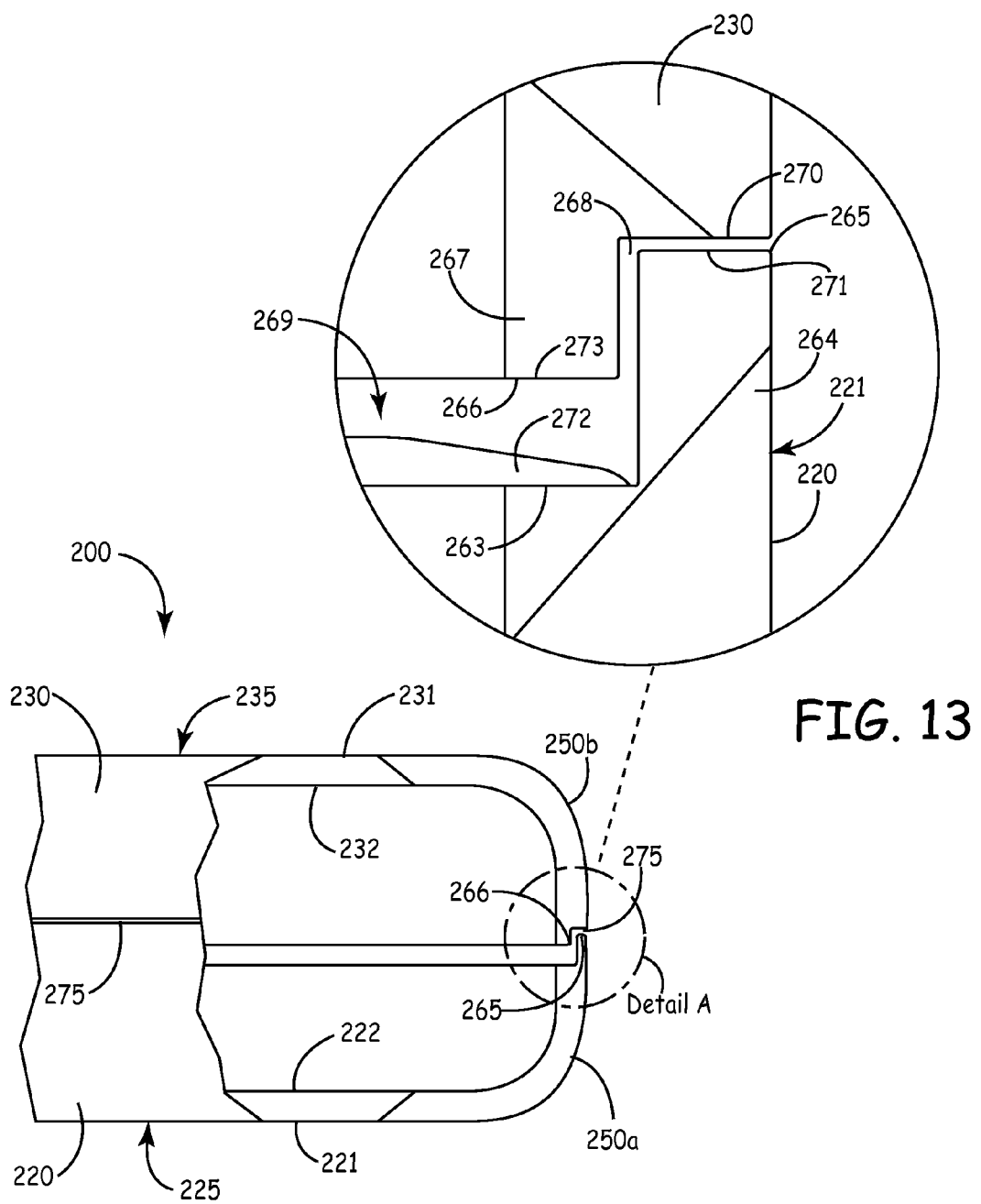
FIG. 12 is a partial cross-sectional view of a housing described herein showing a weld line.
FIG. 13 is an enlarged close up view of Detail A in FIG. 12.

As mentioned previously, the housing 200 is hermetically sealed prior to implantation within a patient. In one embodiment, the second portion 230 is secured to the first portion 220 of the housing in a tight fitting relationship, for example, by laser welding. In one embodiment, a weld is provided about the entire perimeter of the housing 200 where the sidewall 250a of the first portion 220 mates with the sidewall 250b of the second portion 230. In general, the housing is welded along peripheral edges 265, 266 of the first 220 and second 230 portions. FIG. 12 is a partial cross-sectional view of one embodiment of a housing 200 showing a weld line 275. FIG. 13 is an enlarged view of Detail A shown in FIG. 12.

In conventionally "stamped" housings, the sidewalls of the housing proximate the weld line have a substantially uniform thickness and frequently require the use of a weld ring. In contrast, when the housing 200 is formed using a molding process, it is possible to vary the thickness of the sidewalls 250 proximate the weld line 275. This can be beneficial, for example, because the weld line 275 can be configured to reduce the incidence of weld failures and avoid the need for a weld ring, thereby reducing costs, number of parts, steps in manufacturing, improving repeatability of the welding process and reducing stress effects on the material.

In one embodiment, the weld line 275 is configured with one or more mating structures that provide a physical overlap between the two halves of the housing 200. As shown in FIGS. 12 and 13, a weld line 275 is provided around the entire perimeter of the sidewall 250 between the peripheral edges 265, 266 of the first 220 and second 230 portions of the housing 200. In one embodiment, the peripheral edge 265 of the first portion 220 includes a groove 263 and a stepped portion 264, wherein the groove 263 includes a groove surface 272 and the stepped portion 264 includes a stepped portion surface 271. The peripheral edge 266 of the second portion 230 includes a complementary groove 268 having a groove surface 270 and a complementary stepped portion 267 having a stepped portion surface 273. Either the groove 268 or the stepped portion 267 can be disposed radially inward from the outer surface 231 of the second portion 230 of the housing 200. However, it is generally desirable that the groove 268 and the stepped portion 267 of the second portion 230 of the housing 200 are configured to mate with the groove 263 and stepped portion 264 of the first portion 220 of the housing 200.

In one embodiment, the groove 263 of the first portion 220 of the housing 200 is disposed radially inward from the outer surface 221 of the housing 200 and has a height that is greater than the height of the corresponding stepped portion 267 of the second portion 230 of the housing 200, such that a gap 269 is defined along the interior of the housing 200 when assembled. In general, the height of the groove 263 and stepped portion 264 of the first portion 220 of the housing 200 are approximately the same and can be determined by measuring the shortest linear distance between the groove surface 272 and the stepped portion surface 271. Similarly, the height of the groove 268 and stepped portion 267 of the second portion 230 of the housing 200 are approximately the same and can be determined by measuring the shortest linear distance between the groove surface 270 and the stepped portion surface 273. The gap 269 helps improve the alignment of the exterior surfaces 221, 231 of the housing 200 when assembled.

System Components

The implantable device 100 includes an electronics package that includes system components known in the art to carry out the system functions. For example, the device 100 may include one or more pulse generators, including associated batteries, capacitors, microprocessors, and circuitry for generating defibrillation and/or pacing pulses. The positioning of the system components within the housing 200 is highly modifiable although the spatial requirements of the housing 200 may vary depending upon the system components used within the device 100.

Given the minimal space provided to house the system components, it is generally desirable to arrange the components to efficiently use the available space. In one embodiment, the relative positions of one or more system components within the housing are maintained by one or more structural elements positioned within the housing.

In one embodiment, the housing includes one or more structural elements such as those shown in FIG. 14. As used herein, the term "structural element" can refer to an aperture, notch or other indentation provided within the housing in addition to physical structures having various sizes and shapes, such as a block or other shaped protrusion 2299. In another embodiment, the relative positions of one or more system components within the housing are maintained by one or more structural elements that function as spacing elements or spacers. In the embodiment shown in FIG. 14, one example of a physical structure is an elongate structure such as a wall or partition 2300a.

If desired, one or more structural elements 2298, 2299, 2300a can be configured to secure one or more system components to the housing 2200. For example, in one embodiment, the structural element 2298 can includes a block or protrusion having one or more openings or apertures, wherein the aperture or opening is sized to receive one or more corresponding projections present on one or more system components, thereby anchoring that component. However, it is envisioned that in other embodiments, the system components can remain free within the housing (i.e., not secured to the housing). In this embodiment, the system components are typically carefully configured and arranged within the housing to reduce relative movement of the components when the housing is assembled. In yet an alternate embodiment, one or more of the system components may be secured to the interior surface of the housing, for example, by welding, adhesive, pins, screws and the like.

Internal Structural Element

When the device is implanted, the muscles and ribs of the patient put physical pressure on the device, which could in turn put pressure on the system components. Therefore, it may be desirable for the housing to include one or more structural elements that function as supporting structures. As used herein, the term "supporting structure" refers to a structural element that is configured to reinforce the structural integrity of the housing to prevent the housing from flexing or breaking and potentially damaging the system components contained within the housing. In one embodiment, the housing can include one or more structural elements that function both as supporting structures and to maintain the relative positions of one or more system components within the housing.

In one embodiment, one or more structural elements are fabricated separately from the housing and remain free within the housing upon assembly. In another embodiment, the separately fabricated structural elements are secured to an interior surface of the housing in a known manner, including, but not limited to, welding, adhesive, pins, screws and the like. Suitable biocompatible materials for forming a structural element are known and include, for example, plastics and metals. In another embodiment, such as that shown in FIGS. 2-7 and 14-17, one or more structural elements 300, 2300 are integrally formed with the housing 200, 2200.

When one or more structural elements are integrally formed with the housing, the structural element has the additional benefits of reducing manufacturing time and expense and reducing material stress, including warping. Additionally, the use of a molding process provides a significant amount of design freedom in the shape of the structural elements. For example, the cross-sectional profile of one or more structural elements can be varied in ways that is not possible using stamping technology. In the embodiment shown in FIGS. 2-7 and 15-16, one or more structural elements 300 have a proximal end 301, 303 integrally molded with the interior surface 222, 232 of the first 220 or second 230 portion of the housing 200 and an opposing distal end 302, 304. If desired, the cross-sectional profile of one or more structural elements can be tapered such that the cross-section of proximal end is wider than the cross-section profile of the distal end. In other embodiments, the structural elements can include one or more apertures or openings, for example, to facilitate the interconnecting of system components. Alternately, the structural elements can include other design features such as indentations or projections to accommodate the contours of adjacent system components.

In the embodiment shown in FIGS. 14 and 17, the first portion 2220 of the housing 2200 includes one or more structural elements 2300a comprising a proximal end 2301 integrally molded with the interior surface 2222 of the housing 2220 and an opposing a distal end 2302. Similarly, the second portion 2230 of the housing 2200 includes one or more structural elements 2300b that mirror one or more structural elements 2300a of the first portion 2220, wherein the structural elements 2300b of the second portion 2230 have both a proximal end 2303 and a distal end 2304 and the distal end 2304 of one or more structural elements 2300b of the second portion 2230 are configured to align with and contact the distal ends 2302 of one or more structural elements 2300a of the first portion 2220 when the housing 2200 is assembled.

In another embodiment (not shown), the distal end of one or more structural elements of the first portion of the housing is configured to contact the interior surface of the second portion when the housing is assembled. In this embodiment, the height of one or more structural elements (determined by the shortest linear distance between the proximal and distal ends of the structural element) is greater than the height of the sidewall of the first portion. In an alternate embodiment (not shown), the second portion of the housing includes one or more structural elements comprising a proximal end integrally molded with the interior surface of the housing and an opposing a distal end wherein one or more structural elements are configured to contact the interior surface of the first portion when the housing is assembled. Similarly, in this embodiment, the height of one or more structural elements (determined by the shortest linear distance between the proximal and distal ends of the structural element) is greater than the height of the sidewall of the second portion.

In the embodiments shown in FIGS. 2-7 and 14-17, the housing 200 includes one or more elongate structural elements 300. In one embodiment, the one or more elongate structural elements 300 radially extend from an axis substantially perpendicular to the planes defined by the base 225 and top 235 of the housing 200 to form two or more compartments within the housing 200. Even though the axis is located near the center of the housing 200 in the embodiment shown in FIGS. 2-7 and 14-17, it is envisioned that the axis could be located at any position between the center and the perimeter of the housing 200.

Connector Header

As shown in FIG. 1, the device 100 may include a connector header 110 to provide communication between the device circuitry and the leads 104, 106 of the device 100. In one embodiment, one or more leads 104, 106 are removably coupled to circuitry in the housing 200 via a connector header 110. In an alternate embodiment, the leads 104, 106 are permanently attached to the device 100, for example, via a connector header 110 or directly to the housing 200. Typically the header 110 is configured to provide a generally continuously curved periphery consistent with the silhouette of the housing 200 to provide a device 100 with a generally smooth profile.

Generally, the header 110 is constructed by liquefying an inert thermoplastic or thermoset material, introducing the molten material into a mold and allowing the material to harden or cure. As shown in FIG. 1, the header 110 typically defines one or more apertures 111, 112 configured to receive an end 144, 146 of a lead 104,106. The apertures 111, 112 include one or more electrical contacts (not shown) that extend from the header 110 through an opening 357 in the housing 200 configured to accommodate the electrical contacts extending from the header to the internal circuitry (not shown). In one embodiment, the electrical contacts extend through an opening 357 in a wall of the housing 200 via one or more insulated feedthroughs configured for electrical communication to and from the system components disposed within the housing 200.

A connector header having any configuration is suitable for use in connection with the device 100 described herein. Another embodiment of a header 1110 is shown in FIGS. 8-11. In this embodiment, the header includes a top surface 1370 and a bottom surface 1371 connected by exterior sidewalls 1372. In the embodiment shown in FIGS. 8-11, the top surface 1370 of the header 1110 is substantially flat and the sidewalls 1372 are curved such that the exterior surface of the header 1110 is smooth and rounded. Typically the header 1110 includes at least one housing contacting surface 1380. In one embodiment, the housing contacting surface 1380 is substantially planar and configured to adjoin a substantially planar header attachment element 1356 of the housing 1200. In one embodiment, the header 1110 includes an attachment element contacting surface 1381. In the embodiment shown in FIGS. 8-11, the bottom surface 1371 of the header 1110 is the attachment element contacting surface 1381.

In some commercially available devices (not shown), the header is adhered to an indentation constructed within the housing, wherein the indentation and header have reciprocal shapes so that the header fills in the indentation and the overall profile of the device remains smooth. In other commercially available devices, the header is spot welded to a surface of the housing. While effective, these arrangements may have certain disadvantages in certain applications or circumstances. For example, in this arrangement, the housing provides only limited structural support for the header. Even in instances in which the device is not dropped, the forces generated by lead insertion, and at all other stages of manufacturing, shipping, handling, and installation, may generate unwanted stresses.

Header Attachment Element

Figure 15:
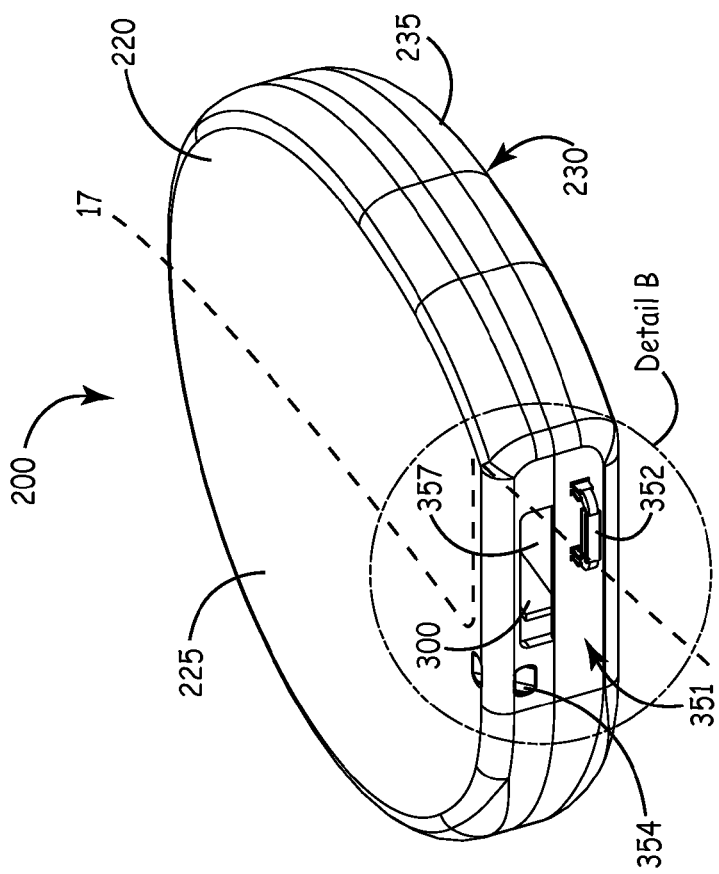
FIG. 15 is a perspective view of a housing having a header attachment element.

In one embodiment, the housing includes a header attachment surface configured to engage a connector header. A first embodiment of a header attachment surface positioned on a header attachment element and is shown in FIGS. 8-11. A second embodiment of a header attachment surface is shown in FIGS. 15 and 16. A third embodiment of a header attachment surface is shown in FIG. 14. Although these embodiments will be discussed in detail below, other embodiments are possible and would be apparent to one of skill in the art upon reading the disclosure provided herein.

The device 1000 shown in FIGS. 8-11 includes a housing 1200 and a header attachment element 1350 extending from the housing 1200. In this embodiment, the header attachment element 1350 is a projection or flange that extends laterally from the housing and has a header contacting surface 1351 configured to receive a connector header 1110 when the device 1000 is assembled and a bottom surface 1355 opposite thereto. In one embodiment, the header attachment element 1350 is integrally molded with and extends from either the first 1220 or second 1230 portion of the housing 1200. In an alternate embodiment, the header attachment element 1350 can be fabricated separately from the housing 1200 and secured thereto using any known method, including but not limited to adhesives, welding, screws, and the like.

In the embodiment shown in FIGS. 8-11, the header attachment element 1350 extends laterally from the housing and is substantially parallel to the plane defined by the base 1225 of the housing 200. In one embodiment, the header attachment element 1350 has a substantially planar header attachment surface 1351. In one embodiment, the header attachment surface 1351 and the bottom surface 1355 of the header attachment element 1350 are substantially parallel such that the header attachment element 1350 is substantially planar. In some embodiments, it may be desirable to have the bottom surface 1355 of the header attachment element 1350 coplanar with the base 1225 of the housing 200. In other embodiments, it may be desirable to have the bottom surface 1355 of the header attachment element 1350 coplanar with the top surface 1235 of the housing, as shown in the FIGS.

In one embodiment, the housing 1200 also includes a header contacting surface 1356, which is configured to contact the housing contacting surface 1380 of the header 1110. In one embodiment, the header contacting surface 1356 of the housing 1200 is substantially planar. Typically, the header contacting surface 1356 of the housing 1200 will define an opening 1357 to accommodate one or more feedthroughs that extend from the header 1110 to the system components contained within the housing 1200.

An alternate embodiment of a header attachment surface is shown in FIGS. 15 and 16. In this embodiment, a header attachment surface 351 is present on the sidewall of the housing. The header attachment surface 351 is substantially planar and extends from the bottom surface 225 of the first portion 220 to the top surface 235 of the second portion 230 of the housing 200. A header that mates with the housing 200 will have a housing contacting surface that is substantially planar to abut the substantially planar header attachment surface 351 of the housing 200. Other embodiments, for example, in which the header attachment surface 351 is coincident with either the top surface 235 or bottom surface 225 of the housing 200 are also possible.

In one embodiment (shown in FIGS. 8-11), the header attachment element 1350 includes a header attachment surface 1351 that includes one or more header attachment structures 1352. The header attachment structures 1352 in this embodiment are pins or cylindrical protrusions extending from the header attachment surface. In an alternative embodiment, the header attachment structures may be one or more openings or apertures (not shown) defined therein.

The structures 1352 are used to align the header 1110 in the proper position on the header attachment element 1350, so that the header can then be permanently joined to the housing. The cylindrical protrusions serve an alignment function, but do not prevent the header from being removed from the header attachment element. In this embodiment, the header 1110 typically includes one or more corresponding apertures 1353 configured to receive the one or more projections 1352 extending from the header attachment surface 1351.

In another embodiment, the header attachment surface includes one or more header attachment structures configured to align and secure a pre-formed header to the header attachment element, which can be referred to herein as "header retaining features." By the term "secure", it is meant that the header cannot be removed from the housing without use of a tool after the structures are engaged with a mating structure on the header. In one such embodiment, the header attachment surface can include one or more structures for securing a pre-formed header with a mating structure, such as mating structures for a snap-fit mechanism or an interference fit mechanism in which the header is secured to the header attachment element by friction after the corresponding structures are engaged. As shown in FIGS. 15 and 16, the header attachment surface 351 may include header attachment structures such as a handle or loop 352 and an opening 354 defined by the housing. A hook-shaped protrusion on the connector header may be inserted into the opening 354, while a snap-fit structure on the header may engage the handle 352.

In addition to the header attachment structures illustrated and discussed herein, there are many other possibilities for mating structures that can serve to align a connector header with a header attachment surface on a housing. There are also many other possibilities for structures that can serve to secure a connector header to a housing.

In some embodiments, a pre-formed header is secured or further secured to the header attachment element, for example, using epoxy, an adhesive, or the like. In yet another embodiment, the header is secured to the housing by inserting a header attachment element into a cavity of a pre-formed header that is configured to receive the header attachment element. In yet another embodiment the header is retained in place by applying the molten material to the header attachment element and molding the header about the header attachment element during construction of the device. In this embodiment it may be desirable to include one or more openings, such as tapered openings in the header attachment element (not shown) configured to receive the molten header material, such that when the header material hardens, the header is secured to the header attachment element at least in part by the connection of the header material to the one or more tapered openings.

If desired, the header attachment element 1350 can define one or more openings to provide one or more suture anchoring locations 1360 for securing the implanted device 1000 when implanted in a patient as shown in FIGS. 8-11. In this embodiment, it may be desirable to have a connector header 1110 having an attachment element contacting surface 1381 that includes one or more indentations configured to align with one or more suture anchoring locations 1360 in the header attachment element 1350 to provide sufficient room for suture placement during implantation.

A third embodiment of a header attachment surface is shown in FIG. 14, where a cylindrical protrusion 2352 extends from a header attachment surface, and serves as a header attachment structure. The cylindrical protrusion 2352 is configured to interface with an opening on a connector header, to align the connector header for attachment to the housing 2200.

Molding Processes

As used herein, the term "molding" refers to a process of manufacturing in which a pliable raw material is shaped using a pattern or mold having a desired size and shape. Typically, the mold defines a cavity that is configured to receive a flowable material such as a liquefied or molten metal or metal alloy. After the flowable material is introduced into the mold, it is allowed to harden and adopt the shape of the mold. After the material hardens, the final product is removed from the mold. Many molding processes are known and include, but are not limited to: injection molding, compression molding, transfer molding, extrusion molding, rotational molding, and the like. Briefly, in an injection molding process, the flowable material is forced into a mold cavity where it cools and hardens to the configuration of the mold cavity. In a compression molding process, the molding material is generally placed in an open mold cavity which is then closed with a top force or plug member and pressure is applied to force the material into contact with all mold areas. In a transfer molding process, the molding material is preheated and loaded into a chamber. A plunger is then used to force the material from the chamber through channels known as a sprue and runner system into the mold cavities. The mold remains closed as the material is added and is opened to release the molded component. In an extrusion molding process, the material is heated and then loaded into a die or container. A ram then presses the material to push it out of the die. In a rotational molding process the mold is slowly rotated (usually around two perpendicular axes) causing the material to flow into to the mold and adhere to the walls of the mold.

Molding processes for both non-amorphous (or crystalline) metals or metal alloys and amorphous metal alloys are known. One process for molding metals includes Metal injection molding or (MIM). In a metal injection molding process, fine metal powders are combined with plastic binders which allow the metal to be injected into a mold using equipment similar to plastic injection molding machines. After the part is molded, the next step is to remove the binders, typically with solvents and/or thermal processes. The resultant metal part is sintered at temperatures great enough to bind the particles but not melt the metal. Another process for molding amorphous metal alloys includes the process provided by LiquidMetal Technologies of Rancho Santo Margarita, Calif. One advantage of the non-amorphous molding process is that the molding process generally results in a final product having a very small volume change (less than about 0.5%) as compared to the mold.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of a molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. An implantable medical device, comprising:
(a) a metal housing comprising:
  (i) a first portion having a base and one or more sidewalls wherein the base and sidewalls each have an interior surface and an exterior surface and wherein the interior surfaces of the base and sidewalls define a cavity;
  (ii) a second portion configured to enclose the cavity defined by the first portion when the housing is assembled, wherein the first and second portions are capable of being hermetically sealed to isolate the cavity defined by the housing from an external environment and the housing defines an opening configured to accommodate one or more feedthroughs extending from a header located external to the cavity defined by the sidewalls;
  (iii) one or more elements selected from the group consisting of: a header attachment element integrally molded with and extending from the exterior surface of the first or second portion of the housing, the header attachment element comprising a header attachment surface with one or more header attachment structures configured to mate with a connector header; a header attachment surface integrally molded with the first or second portion of the housing and on the exterior surface of the first or second portion of the housing, the header attachment surface comprising one or more header retaining features configured to secure the connector header to the header attachment surface; one or more structural elements extending from and integrally molded with the interior surface of the first or second portions of the housing, and combinations thereof; and
(b) an electronic package configured to be disposed within the housing.

2. The implantable medical device of claim 1, the header attachment element comprising the header attachment surface with one or more header attachment structures configured to mate with the connector header.

3. The implantable medical device of claim 2, wherein the base of the first portion is planar and the header attachment element is substantially parallel to the plane defined by the base.

4. The implantable medical device of claim 3, wherein the header attachment element is substantially coplanar with the plane defined by the base of the housing.

5. The implantable medical device of claim 2, wherein one or more header attachment structures comprise one or more projections configured to align the connector header with the header attachment element during assembly.

6. The implantable medical device of claim 5, wherein the connector header defines one or more openings configured to receive the projections.

7. The implantable medical device of claim 6, wherein the one or more projections are cylindrical.

8. The implantable medical device of claim 2, wherein the housing comprises a header contacting surface that defines one or more openings to accommodate one or more feedthroughs extending from the connector header.

9. The implantable medical device of claim 1, comprising the header attachment surface comprising one or more header retaining features configured to secure the connector header to the header attachment surface.

10. The implantable medical device of claim 9, wherein one or more header retaining features include a handle-shaped projection.

11. The implantable medical device of claim 1, wherein the first portion includes one or more of the integrally molded structural elements comprising a proximal end integrally molded with the interior surface of the first portion and an opposing a distal end; and the second portion includes one or more or the integrally molded structural elements comprising a proximal end integrally molded with the interior surface of the second portion and an opposing distal end, wherein the distal end of the one or more structural elements of the second portion align with and contact the distal ends of the one or more structural elements of the first portion when the housing is assembled.

12. The implantable device of claim 11, wherein the electronics package comprises a plurality of system components disposed within the housing having positions relative to one another and one or more structural elements are configured to maintain the relative positions of the system components of the electronic package within the housing.

13. The implantable device of claim 11, wherein the first portion has a substantially planar base and the second portion has a substantially planar top, wherein the planar base and the planar top are substantially parallel.

14. The implantable device of claim 11, wherein one or more structural elements comprise one or more elongate structural elements radially extending from an axis substantially perpendicular to the planes defined by the base and the top of the housing.

15. A method of making the implantable medical device of claim 1, the method comprising:
    (a) preparing a mold defining the first and second portions of the housing; and
    (b) molding the first and second portions with a molten metal alloy.

16. The method of claim 15, further comprising the steps of:
    assembling the first and second portions to form the housing;
    fabricating the connector header; and
    securing the connector header to the header attachment element.

17. The method of claim 15, further comprising the step of molding a connector header onto the header attachment element of the housing.

\* \* \* \* \*